(12) United States Patent
Bublitz et al.

(10) Patent No.: US 8,289,382 B2
(45) Date of Patent: Oct. 16, 2012

(54) METHOD FOR PRODUCING HIGH-QUALITY REPRODUCTIONS OF THE FRONT AND/OR REAR SECTIONS OF THE EYE

(75) Inventors: Daniel Bublitz, Jena (DE); Thomas Mohr, Jena (DE); Uwe Mohrholz, Jena (DE); Michael Trost, Stadtroda (DE); Martin Wiechmann, Jena (DE); Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 615 days.

(21) Appl. No.: 12/517,414

(22) PCT Filed: Nov. 24, 2007

(86) PCT No.: PCT/EP2007/010228
§ 371 (c)(1),
(2), (4) Date: Jun. 3, 2009

(87) PCT Pub. No.: WO2008/067922
PCT Pub. Date: Jun. 12, 2008

(65) Prior Publication Data
US 2010/0060728 A1    Mar. 11, 2010

(30) Foreign Application Priority Data
Dec. 5, 2006    (DE) .......................... 10 2006 057 190

(51) Int. Cl.
*H04N 7/18* (2006.01)
(52) U.S. Cl. ............................................ 348/78; 348/67
(58) Field of Classification Search .......... 348/370–376, 348/67, 77–78; 396/173, 176
See application file for complete search history.

(56) References Cited

U.S. PATENT DOCUMENTS

| | | | |
|---|---|---|---|
| 4,357,083 A | 11/1982 | Johnson et al. | |
| 4,589,754 A | 5/1986 | Maitani et al. | |
| 4,589,755 A | 5/1986 | Maitani et al. | |
| 4,589,757 A | 5/1986 | Maitani et al. | |
| 4,618,238 A | 10/1986 | Maitani et al. | |
| 4,998,128 A | 3/1991 | Coltman et al. | |
| 5,557,321 A | 9/1996 | Kohayakawa et al. | |
| 6,094,536 A | 7/2000 | Harada | |
| 6,151,073 A | 11/2000 | Steinberg et al. | |
| 6,714,665 B1 * | 3/2004 | Hanna et al. .................. | 382/117 |
| 6,922,528 B2 | 7/2005 | Okabe | |
| 7,428,378 B1 * | 9/2008 | Warpakowski Furlan .... | 396/157 |
| 7,589,784 B2 * | 9/2009 | Chiba et al. .................. | 348/371 |
| 7,792,378 B2 * | 9/2010 | Liege et al. .................. | 382/254 |
| 2002/0088952 A1 * | 7/2002 | Rao et al. ................. | 250/559.45 |
| 2004/0109082 A1 * | 6/2004 | Yokonuma .................... | 348/371 |
| 2004/0114796 A1 * | 6/2004 | Kaku ............................ | 382/165 |
| 2006/0238832 A1 * | 10/2006 | Ohsawa ........................ | 358/518 |
| 2007/0236567 A1 * | 10/2007 | Pillman et al. ................ | 348/143 |
| 2007/0253694 A1 * | 11/2007 | Miyazawa et al. ............ | 396/234 |
| 2008/0252731 A1 * | 10/2008 | Blais-Ouellette et al. .... | 348/162 |

FOREIGN PATENT DOCUMENTS

| | | |
|---|---|---|
| DE | 31 39 547 | 4/1982 |
| DE | 33 32 835 | 6/1984 |
| DE | 33 47 872 | 6/1987 |
| DE | 690 26 826 | 12/1996 |
| DE | 102 42 851 | 4/2004 |
| DE | 10 2004 011 906 | 9/2004 |
| EP | 0 512 508 | 11/1992 |
| EP | 1 457 154 | 9/2004 |
| WO | WO 2006/016366 A2 | 2/2006 |
| WO | WO 2006/016366 A3 | 2/2006 |

* cited by examiner

*Primary Examiner* — Joshua Joo
(74) *Attorney, Agent, or Firm* — Frommer Lawrence & Haug LLP

(57) ABSTRACT

The present invention makes it possible to make high-quality recordings of the anterior and/or posterior segments of the eye as an individual image or also as a sequence of images without increasing the radiation load on the eye to be examined. In the method according to the invention, at least one pre-flash is used in order to determine an optimal exposure time for the main flash based on the recording of the pre-flash which is reflected by the object to be recorded. Both the pre-flash and the main flash are controllable and the recordings of the pre-flash and main flash are recorded with the same sensor of the electronic camera and are evaluated electronically by a control unit, and the recording of the main flash and, as the case may be, of the pre-flash is analyzed and/or corrected and displayed to the user.

12 Claims, No Drawings

METHOD FOR PRODUCING HIGH-QUALITY REPRODUCTIONS OF THE FRONT AND/OR REAR SECTIONS OF THE EYE

The present application claims priority from PCT Patent Application No. PCT/EP2007/010228 filed on Nov. 24, 2007, which claims priority from German Patent Application No. DE 10 2006 057 190.8 filed on Dec. 5, 2006, the disclosure of which is incorporated herein by reference in its entirety.

BACKGROUND OF THE INVENTION

1. Field of the Invention

The present invention is directed to a solution which makes it possible to make high-quality recordings of the anterior and/or posterior segments of the eye as an individual image or also as a sequence of images without increasing the radiation load on the eye to be examined.

2. Description of Related Art

According to the known prior art, flash lamps are used in fundus cameras and slit lamps to illuminate the relevant areas of the eye for achieving recordings of correspondingly high quality. Observation and documentation are carried out in this case by means of an electronic camera.

Depending on the area of the eye to be illuminated, the exposure must be controlled exactly, because too much light leads to over-illuminated images and too little light leads to images with poor contrast and high noise. Optimal illumination data are made even more difficult to achieve in that these data vary for the different recording modes (monochrome recordings, color recordings or fluorescence recordings). The illumination intensity can vary owing to variations in the spectral composition of the illumination light, the size of the ring illumination, or the width of the slit illumination.

Additional factors influencing optimal exposure, aside from the individual differences between the illuminated objects (pupil size, reflection factor of the retina, cornea and lens), include individual differences in opthalmological instruments (optical characteristics of the components used, differences in component assemblies, tolerances, aging, soiling, etc.).

Not least of all, individual user requirements such as, e.g., gradual overexposure or underexposure should be taken into account in the optimal exposure or, more precisely, in achieving the optimal signal-to-noise ratio for the electronic image recording.

Solutions to these problems are known in the prior art in which multiple recordings are made by the user and the exposure time is successively, individually adapted. The disadvantage consists in the high, repeated radiation load on the patient's eye. In other known solutions, a portion of the reflected light is coupled out of the observation beam path, integrally summed, and used for controlling the flash. Otherwise, the user accepts recordings which are not optimal.

DE 10 24 2851 A1, DE 10 2004 011 906 A1, and EP 0 512 508 B1 describe solutions for controlling the flash exposure in photographic cameras. The exposure is measured during the recording through the objective (TTL=Through The Lens) and works with a pre-flash in the visible range and associated electronic evaluation. The light measurement is carried out zone by zone, a photodiode being provided for the central measurement and an array for measuring the ambient light. The pre-flash is automatically repeated as needed. Apart from the visible pre-flash and the evaluation merely zone-by-zone in partial areas, it is also disadvantageous that a photodiode and an array of photodiodes are additionally required.

DE 31 39 547 C2 and DE 33 32 835 C2 describe a solution for exposure control in a photographic camera or a device for advance information about a photographic flash exposure which work with a pre-flash in the visible range and associated electronic evaluation. The visible pre-flash and merely zonewise evaluation requiring an additional photodiode are disadvantageous.

DE 33 47 872 C2 describes a photographic camera with spot exposure measurement and integral exposure measurement in which the light measurement is carried out zone by zone. In addition, a photodiode is provided for the center spot measurement and a second photodiode is provided for measuring the ambient light. It is disadvantageous that the evaluation is only carried out zone by zone.

A pre-flash method in which an integral light measurement is carried out with only one photocell is described in DE 690 26 826 T2. It is disadvantageous that the evaluation which is only carried out point by point requires additional photodiodes or an array of photodiodes. Further, with integral measurement of the light energy very small areas of the recording can be over-illuminated already when the predominant, residual image area of the recording is dark. Therefore, an integral measurement of the light intensity while the picture is being taken is unsuitable particularly for slit recordings.

Solutions of the kind mentioned above with visible pre-flashes and/or multiple recordings have the disadvantage of very high radiation loading of the patient's eye.

In order to give calculated light outputs accurately, flash lamps with reproducible flash output are required and must be controlled by an elaborate flash control with switch-on and switch-off delays having an accuracy in the range of about 50 µs.

Since the pre-flash and principal recording are generally evaluated separately, a plurality of light-sensitive sensors are required.

For example, in the system for flash photography described in U.S. Pat. No. 6,094,536 A, a separate light-sensitive sensor is also used for light measurement. The solution for determining the data for a main flash is based on the evaluation of a light measurement of a first flash of constant intensity and a light measurement of the environment without flash illumination. In this way, not only the amount but also the constant intensity of the flash output is controllable over a given period of time.

A fundus camera with a flash lamp for realizing recordings of an eye is described in U.S. Pat. No. 5,557,321 A. The proposed system has two image recording devices of different sensitivity. One image recording device carries out low-resolution overview recordings and the other image recording device carries out high-resolution detailed recordings. The light output emitted by the flash lamp is matched to the appropriate sensitivity. This solution has the drawback that two photographic systems are required, which makes the overall construction of the fundus camera more complicated and expensive.

SUMMARY OF THE INVENTION

It is the object of the present invention to develop a solution which makes it possible to carry out high-quality recordings of the anterior and/or posterior eye segments in which stress on the patient, particularly high radiation loads, is avoided. But, aside from achieving an optimal signal-to-noise ratio for the electronic image recordings, individual user requirements such as, e.g., gradual overexposure and underexposure in determining the optimal exposure are also taken into account.

According to the invention, this object is met through the features of the independent claims. Preferred further developments and embodiments are the subject matter of the dependent claims.

In the method according to the invention for generating high-quality recordings of the anterior and/or posterior eye segments, at least one pre-flash is used in order to determine an optimal exposure time for the main flash based on the recording of the pre-flash which is reflected by the object to be recorded, wherein both the pre-flash and the main flash are controllable and the recordings of the pre-flash and main flash are recorded with the same sensor of the electronic camera and are evaluated electronically by a control unit, and the recording of the main flash and, as the case may be, of the pre-flash is analyzed and/or corrected and displayed to the user. In an advantageous embodiment, the pre-flash is generated by a separate radiation source, preferably in the infrared range.

The solution for generating high-quality recordings of the anterior and/or posterior eye segments is provided for opthalmological instruments, particularly slit lamps and fundus cameras.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

In the method according to the invention for generating high-quality recordings of the anterior and/or posterior eye segments, at least one pre-flash is used in order to determine an optimal exposure time for the main flash based on the recording of the pre-flash which is reflected by the object to be recorded, wherein both the pre-flash and the main flash are controllable and the recordings of the pre-flash and main flash are recorded with the same sensor of the electronic camera and are evaluated electronically by a control unit, and the recording of the main flash and, as the case may be, of the pre-flash is analyzed and/or corrected and displayed to the user. Both the pre-flash and the main flash are generated by a radiation source based on an electrical discharge or based on a high-power semiconductor emitter, wherein the radiation load of pre-flash to main flash differs substantially, roughly in a ratio of greater than 1:4.

Simple, inexpensive flash lamps with a relatively high individual dispersion of the radiation output in the range of up to ±50% can be used as a radiation source. The dispersion of the radiation output can result from the component dispersion of the flash lamps, type dispersion between alternate suppliers, relatively extensive aging, or the like. However, it is crucial that the radiation source has a relatively good reproducibility of radiation output of less than +/−10% between the pre-flash and main flash.

Since the dimensioned lifetime of the radiation source is generally shorter than the lifetime of the opthalmological instrument, a fast, easy exchanging of the radiation source must be taken into account.

Lasers in which the dispersions of the radiation output are correspondingly low can also be used as a radiation source.

The accuracy of the optimal exposure time to be calculated can be further increased by using a plurality of pre-flashes. The flash rate should be high enough (>60 Hz) that the patient cannot distinguish the individual flashes. Further, at least one parameter (e.g., flash length) should be variable, and the total light energy of one pre-flash is preferably distributed over a plurality of pre-flashes so as not to increase the total radiation load on the patient.

In a first advantageous embodiment, the pre-flash is generated by a separate radiation source, preferably in the infrared range, and the radiation load of pre-flash to main flash differs substantially, roughly in a ratio of greater than 1:10. Further, there is no radiation load on the patient's eye in the visible range. The radiation sources which are used image on the same aperture.

The infrared radiation source used preferably has a highly reproducible radiation output. Through the use of an additional infrared radiation source in the form of a high-power infrared LED, the exposure time for the pre-flash can also be considerably longer, namely, up to 50 ms.

The pre-flash should cause the least possible radiation stress on the patient, i.e., it should be a very short, defined pre-flash by the flash lamp or preferably use of the infrared component of a pre-flash of the flash lamp.

For this purpose, a high-power infrared LED by OSRAM with a cw power of 0.5 W to 5 W can be used, for example. The radiation energy for the pre-flash can be controlled individually by a separate actuation of the infrared radiation source so that there are, for example, 16 flash stages.

It is possible to record a plurality of infrared pre-flashes with optionally variable radiation energy of the infrared radiation source and calculation of the exposure time based a plurality of data sets to determine the exposure time with greater accuracy. Further, it is possible to operate the infrared radiation source in cw mode in order to carry out corresponding pre-adjustments and to position the opthalmological instrument optionally with respect to the patient's eye.

In a second advantageous embodiment, the illumination radiation of the pre-flash and that of the main flash are homogenized, for example, by means of an optical integrator rod or microlens array.

In this way, mechanical tolerances of the flash lamp, tolerances in the shaping of the light arc, and tolerances of the mechanical installation can be compensated. Optionally, the homogenization could also serve to homogenize the light of a plurality of flash lamps which could be actuated individually or simultaneously.

This implementation is advantageous because there is already a reserve flash lamp fixedly installed by the supplier of the opthalmological instrument and in the event of failure of the first flash lamp it is only necessary to switch to the reserve flash lamp. The user is informed of the failure so that it is possible to continue working without restrictions. The defective flash lamp is routinely replaced during the next servicing.

The measurement of the actual recording conditions is carried out in that an overview recording of the individual illumination situation is made in a spatially resolved manner by means of a pre-flash with defined radiation energy and a relatively short exposure time and is evaluated by the control unit. The reflected light is recorded with the sensor of the electronic camera preferably in the infrared range at a very low resolution of, for example, 120×160 pixels so that the time for determining the optimal exposure period for the main flash can be substantially reduced. The resolution of the recording of the pre-flash can be reduced while retaining the information for evaluating the exposure, for example, by combining a plurality of pixels to form segments and subsequently evaluating the segments.

To further accelerate the determination of the optimal exposure time for the main flash, it is also possible to use special cameras in addition to reducing the resolution of the recording of the pre-flash. For example, the recorded analog image data is processed substantially faster by cameras with more than one analog-to-digital converter (so-called high-speed cameras) or cameras with a plurality of sensors such as, e.g., 3-chip cameras, with spectrally selective R/G/B sensors.

The optimal exposure period is calculated by searching for the brightest pixels in the pre-image and determining the difference with respect to their maximum level. Preferably, at least five contiguous pixels are determined as brightest pixels. This has the advantage that the pixel defects (completely inactive or damaged to varying degrees) typically present in the sensors do not falsify the results of the calculation.

Further, the maximum limiting value for the radiation load on the eye to be illuminated is taken into account in the calculation of the optimal exposure time for the main flash so that there is a safety margin of at least 10%. Another safety margin which takes into account tolerances of structural component parts and computing tolerances as well as differences between the pre-recording and the main recording is ensured by calculating the exposure time in such a way that the brightest pixel is controlled to a maximum of 70%. Accordingly, the occurrence of over-illuminated image areas in the electronic recording is virtually eliminated. When the tolerances of the rest of the parameters are relatively low, the margin can be reduced to 2%.

The image recording is carried out with optimum exposure in that the main flash is actuated with a calculated optimum exposure time, and the light reflected by the areas to be illuminated is recorded by the sensor of the electronic camera and analyzed and/or corrected by the control unit. The quality of the recorded image is checked against appropriate criteria. In this connection, the controlling of the light output of the main flash having a duration of up to 10 ms can be carried out in different ways:
1. Time-controlled flash: The flash lamp is switched off when the optimal exposure is achieved or after a defined time.
2. Charge monitoring: Switched off when a defined discharge state of the flash capacitor is reached or, when semiconductor light sources are used, by varying the current through the source.
3. Optical shutter: The illumination beam path is blocked when the optimal exposure is reached.

By analyzing the results, the quality of the recorded image is checked against suitable criteria such as, for example, by searching for over-illuminated pixels. Optionally, the recorded image can be post-processed electronically by a precision correction by means of software. In this way, existing backups can be used, for example, correction or optimization of contrast. In this regard, it may be advantageous when the image quality is improved automatically by an adaptive algorithm.

The analysis of the quality of the recorded images can also be carried out by evaluating pixel information in the form of histograms which contain the statistical distribution of the brightness information or by assessing the differences in contrast in images with different illumination. The average brightness of the pixels which are not over-illuminated is evaluated, for example, for expanding dynamics.

In contrast, in order to analyze the quality of recorded slit images the opthalmological image contents are extracted and assessed.

To correlate images when correcting for displacement and for quantifying motion blurring, Fourier-transformed images are required. The transformation of the images then depends on the spatial frequencies contained in the image. A histogram of the spatial frequencies then shows higher values for the spatial frequencies, for example, in a "sharper" image.

An advantage of individually controlling the radiation energy is the use of an electronic camera that need not necessarily have a global shutter. Accordingly, it is also possible to use cameras with rolling shutters which have a higher sensitivity and, in case of CCD displays, also a better color fidelity.

The camera preferably has a nonlinear brightness function which is adapted to the curve of the human eye. This ensures that the electronic recordings of the camera coincide with the image impression from a direct observation. Direct observation of the anterior and/or posterior eye segments is carried out, e.g., by means of a split lamp microscope or direct opthalmoscope.

In an automated method step, the recording of the main flash is analyzed and/or corrected by the control unit with calculated, optimal exposure time in that the quality of the recorded image is checked against suitable criteria. When needed, the recordings are electronically post-processed to achieve an optimum image quality.

In an advantageous manner, a subsequent determination of the optimal exposure time is carried out based on the flash recording and a comparison to the originally determined exposure time resulting in an adaptive algorithm and automatic improvement in image quality.

In another advantageous method step, the different dynamics in the pre-image and main image are taken into account to enhance contrast in that the quotient of the radiation energies of both images is exactly determined, the over-illuminated pixels of the brighter image are replaced with the corresponding pixels of the darker image, and the brightness of the pixels of the darker image are corrected by the exactly determined factor of the difference in brightness. The quotient of the radiation energies between the two recordings can be known by controlling the source or can be determined by an additional highly dynamic detector which is not spatially resolved or from the sum of all of the pixel values which are not oversaturated in the two recordings.

Based on partial images which are selected from the two recordings and correlated with one another, possible displacements of the image contents between the recordings can be determined and corrected. The selected partial images may not be oversaturated or undersaturated.

For example, the fixedly adjusted ratio of the radiation energy of pre-image to main image is 1:16, i.e., the much brighter main image is recorded with 16-times higher radiation energy. The radiation energy is the product of radiation output and irradiation time. Both the irradiation time and the radiation output can be varied between the main image and the pre-image depending on the technical design. It must be ensured that the longest exposure time is short enough to prevent motion blurring in one of the recordings.

First, a matching image area is determined in the two images. The difference in the radiation energy of the two images, for example, a factor of 15.2, is exactly determined at this image area. A recording is then combined from the two images which takes into account all pixels from the bright image which are not overexposed. The over-illuminated pixels of the bright image are replaced by pixels from the darker image. The brightness of the pixels of the darker image is corrected by the exactly determined factor of the brightness difference which is 15.2 in the present example. In this method of contrast enhancement, a sensor is preferably used which can store the image information temporarily so that the pre-image and main image can be recorded at a very brief interval of, e.g., a maximum of 10 ms. After the recording, the pre-image and main image are digitally converted and fed to the control unit. The method described herein can also be implemented with two or more pre-images and a main image, in which case there is a factor of 2 to 20 between the radiation energies of the recordings, e.g., three recordings. In this way, recordings with an even higher dynamic can be achieved.

If there is too much time between two recordings in image sequences of this kind, the image contents can change and/or be displaced in the meantime. In this case, an image section which is neither undersaturated nor oversaturated is selected in each of the two images. These image sections are then correlated with one another to determine the displacement between the recordings and to compensate for the displacement in the recordings. If this process is repeated for all successive image pairs of a sequence, more than two images can also be corrected for displacement so as to form one highly dynamic recording. Optionally, the displacement between successive recordings especially can also be corrected with an optical image stabilizer.

When using a sensor which is light-sensitive during the readout of the image information, it is preferable to switch off the radiation source during the readout.

In an advantageous method step, partial areas of the flash lamp are shadowed in the beam path. For example, a diaphragm, with variably controllable diameter or a device with a variable, adjustable degree of gray shading such as an LCD display is used for this purpose. This function is advantageous for fundus cameras, for example. In this regard, interfering reflections and scattered light at the cornea and iris of the eye can be efficiently reduced by shadowing in the aperture plane of the illumination ring in the form of a diaphragm which reduces the diameter.

In another advantageous construction, the radiation of the illumination beam path is spectrally selected by optical filters to provide corresponding recordings for various diagnostic purposes, for example, fluorescence recordings or infrared recordings or RGB recordings. Swivellable optical filters which are swiveled into the observation beam path, for example, for fluorescence examinations can also be provided for visual observation of special effects.

Opthalmological examining instruments preferably use a radiation source which contains all of the required spectra in total. The individual spectra required for the specific examinations are selected by optical filters in the illumination beam path and combined with the required filters in the observation beam path.

To further optimize the image of the main flash, it may be advantageous to use structures typically having a very high reflection factor such as, for example, the papilla at the retina or the cornea incision when using a slit lamp by evaluating the brightness of these typical structures.

Accordingly, an optimized image is displayed to the user at the end of the process.

A color-selective dynamic expansion can also be used in an advantageous manner. In sequential recordings which are made with monochromatic radiation sources, it is useful for enhancing dynamics to adapt the light energy of each radiation source individually to the output capacity of the radiation source. For example, if the output of green LEDs is not as strong as blue LEDs (approximately twice as much power), a ratio for the radiation output of pre-flash to main flash of 1:8 for the green LED and of 1:16 for the blue LED would be reasonable.

A contrast-selective and color-selective dynamic expansion can also advantageously be used. Generally, the selected radiation period should be as short as possible so that any movements of the object do not lead to blurring in the recording. For example, a radiation period of 1 ms is usual in fundus photography, but the radiation period can be adapted to the contrast of the object in sequential recordings with monochromatic radiation sources. Since fundus recordings are very high in contrast in the green region and very low in contrast in the blue region, the radiation period of the blue LEDs can be selected so as to be longer than the radiation period of the green LEDs (e.g., green LED=1 ms; blue LED=4 ms).

In therapeutic laser coagulation, no usable documentation is possible because of the drastic overexposure of the CCD sensor due to the laser flashes when using conventional recording technology. Therefore, in retinal laser coagulation individual laser parameters are usually set subjectively by the doctor. The whitening of the retina in the respective coagulation spot has been used thus far as a criterion. However, the neuronal sensors located over the pigment epithelium to be treated were disturbed as a result.

By detecting very small changes in the backscattering of the laser beam at the retinal tissue, it would be possible to prevent destruction of the neuronal sensors. Further, this would result in a more accurate adjustment and control of the individual laser parameters.

In another embodiment, the proposed method according to the invention can be used to detect very small changes in the backscattering of the laser beam at the retinal tissue. For this purpose, a pre-flash and a plurality of main flashes at intervals are carried out during the laser treatment. The recordings of the main flashes are analyzed by a control unit, stored, displayed to the user and used in particular for controlling and/or assessing the laser treatment. It is advantageous when the main flashes are carried out during the laser treatment with such short time intervals that the recordings of the main flashes form a video sequence or are at least synchronous to every nth image of a video sequence.

This method can be used not only for laser coagulation but also for so-called grid coagulation in which two-dimensionally extending coagulation spots are lined up for treating pathological retinal areas.

In a particularly advantageous development, the results of the method according to the invention can be used to assess the quality of the coagulation even during the laser treatment. However, it is also possible to adapt the laser output for the next spot in a corresponding manner or to interrupt the laser treatment when predetermined limits are reached.

Since, in particular, the sites to be treated are evaluated and the progress of the coagulation is electronically assessed, an active monitoring of the relevant data for the treatment is carried out so that it is possible to actively control the coagulation.

The special advantage of the proposed method according to the invention for generating high-quality recordings of the anterior and/or posterior eye segments consists in the very low radiation load on the patient's eye, in avoiding unnecessary recordings, and in that the patient is not needlessly troubled by unnecessary light stress in the visible region.

The method allows the use of inexpensive flash lamps which have a high individual dispersion in component characteristics and which possibly change characteristics relatively drastically over their lifetime and, combined with this, simple and economical control electronics. Nevertheless, through the evaluation of the pre-flash and the determination of an optimal exposure time, recordings of the retina, lens, cornea, portions of the visual field, and slit recordings can always be achieved with a very good signal-to-noise ratio.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for generating high-quality recordings of anterior and/or posterior eye segments, comprising:
    using at least one pre-flash to determine an optimal exposure time for a main flash based on a recording of the pre-flash which is reflected by an object to be recorded;
    capturing recordings of the pre-flash and main flash with a same sensor of an electronic camera and evaluating the recordings electronically by a control unit; and
    analyzing and/or correcting, storing, and displaying the recording of the main flash;
    wherein both the pre-flash and the main flash are controllable;
    wherein the optimal exposure time for the main flash is determined such that brightest pixels are searched for in a pre-image and a difference with respect to a maximum level of the brightest pixels is determined; and
    wherein at least five contiguous pixels are determined as the brightest pixels in order to rule out individual pixel errors.

2. A method for generating high-quality recordings of anterior and/or posterior eye segments, comprising:
    using at least one pre-flash to determine an optimal exposure time for a main flash based on a recording of the pre-flash which is reflected by an object to be recorded;
    capturing recordings of the pre-flash and main flash with a same sensor of an electronic camera and evaluating the recordings electronically by a control unit; and
    analyzing and/or correcting, storing, and displaying the recording of the main flash;
    wherein both the pre-flash and the main flash are controllable; and
    wherein the optimal exposure time for the main flash is determined based on a maximum limiting value for a radiation load on an eye to be illuminated, so as to provide a safety margin.

3. A method for generating high-quality recordings of anterior and/or posterior eye segments, comprising:
    using at least one pre-flash to determine an optimal exposure time for a main flash based on a recording of the pre-flash which is reflected by an object to be recorded;
    capturing recordings of the pre-flash and main flash with a same sensor of an electronic camera and evaluating the recordings electronically by a control unit; and
    analyzing and/or correcting, storing, and displaying the recording of the main flash;
    wherein both the pre-flash and the main flash are controllable; and
    wherein the method further comprises adjusting contrast based on different dynamics in a pre-image and a main image such that the adjusting the contrast includes:
    determining a quotient of radiation energies of both the pre-image and the main image;
    replacing over-illuminated pixels of a brighter image with corresponding pixels of a darker image; and
    correcting brightness of the pixels of the darker image by an exactly determined factor of a difference in brightness.

4. The method according to claim 3;
    wherein the quotient of the radiation energies between the pre-image and the main image is known by controlling a source, or is determined by an additional highly dynamic detector which is not spatially resolved or from a sum of all pixel values which are not oversaturated in the recordings of the pre-flash and main flash.

5. The method according to claim 3, comprising:
    selecting partial images which are neither oversaturated nor undersaturated from the recordings of the pre-image and the main image; and
    correlating the selected partial images with one another to determine and correct any possible displacements of image contents between the recordings.

6. The method according to claim 3, further comprising:
    making more than two recordings which differ in illumination intensity by a factor of at least 4;
    determining a quotient of the radiation energies of two successive recordings from a sum of all pixel values which are not oversaturated in the two recordings; and
    determining a highly dynamic image by repeating the quotient determining step for the two successive recordings a number of times.

7. The method according to claim 6, further comprising:
    correcting all successive image pairs for displacement before forming the quotient for the successive recordings.

8. The method according to claim 3, further comprising:
    correcting a displacement between images by means of an optical image stabilizer.

9. A method for generating high-quality recordings of anterior and/or posterior eye segments, comprising:
    using at least one pre-flash to determine an optimal exposure time for a main flash based on a recording of the pre-flash which is reflected by an object to be recorded;
    capturing recordings of the pre-flash and main flash with a same sensor of an electronic camera and evaluating the recordings electronically by a control unit; and
    analyzing and/or correcting, storing, and displaying the recording of the main flash;
    wherein both the pre-flash and the main flash are controllable; and
    wherein the method further comprises:
    using a pre-flash and a plurality of main flashes at intervals during a laser treatment;
    analyzing recordings of the main flashes by a control unit;
    storing and displaying the recordings of the main flashes; and
    using the recordings of the main flashes for controlling and/or assessing the laser treatment.

10. A method for generating high-quality recordings of anterior and/or posterior eye segments, comprising:
    using at least one pre-flash to determine an optimal exposure time for a main flash based on a recording of the pre-flash which is reflected by an object to be recorded;
    capturing recordings of the pre-flash and main flash with a same sensor of an electronic camera and evaluating the recordings electronically by a control unit; and
    analyzing and/or correcting, storing, and displaying the recording of the main flash;
    wherein both the pre-flash and the main flash are controllable; and
    wherein the pre-flash and the main flash proceed during a laser treatment at a frequency that coincides with a frequency of recordings of a video sequence or form integral fractions with the recording frequency of the video sequence.

11. A method for generating high-quality recordings of anterior and/or posterior eye segments, comprising:
using at least one pre-flash to determine an optimal exposure time for a main flash based on a recording of the pre-flash which is reflected by an object to be recorded;
capturing recordings of the pre-flash and main flash with a same sensor of an electronic camera and evaluating the recordings electronically by a control unit; and
analyzing and/or correcting, storing, and displaying the recording of the main flash;
wherein both the pre-flash and the main flash are controllable; and
wherein, for sequential recordings with monochromatic radiation, a light energy of each radiation source is adapted individually to an output capacity of a monochromatic radiation source for enhancing dynamics.

12. A method for generating high-quality recordings of anterior and/or posterior eye segments, comprising:
using at least one pre-flash to determine an optimal exposure time for a main flash based on a recording of the pre-flash which is reflected by an object to be recorded;
capturing recordings of the pre-flash and main flash with a same sensor of an electronic camera and evaluating the recordings electronically by a control unit; and
analyzing and/or correcting, storing, and displaying the recording of the main flash;
wherein both the pre-flash and the main flash are controllable; and
wherein, for sequential recordings with monochromatic radiation, a radiation period for each radiation source is adapted individually to a contrast characteristic of a monochromatic radiation source for contrast-selective dynamic enhancement.

* * * * *